United States Patent

Berg et al.

[11] Patent Number: 5,100,514
[45] Date of Patent: Mar. 31, 1992

[54] SEPARATION OF PYRIDINE FROM WATER BY EXTRACTIVE DISTILLATION

[75] Inventors: Lloyd Berg, 1314 S. Third Ave., Bozeman, Mont. 59715; Zuyin Yang, Bozeman, Mont.

[73] Assignee: Lloyd Berg, Bozeman, Mont.

[21] Appl. No.: 663,439

[22] Filed: Mar. 1, 1991

[51] Int. Cl.$^5$ .................... B01D 3/40; C07D 213/06
[52] U.S. Cl. ........................ 203/14; 203/57; 203/58; 203/59; 203/60; 203/61; 203/62; 203/63; 203/64
[58] Field of Search ............. 203/14, 64, 59, 58, 203/63, 57, 62, 60, 61; 546/353

[56] References Cited

U.S. PATENT DOCUMENTS

| | | | |
|---|---|---|---|
| 2,058,435 | 10/1936 | Fisher | 203/14 |
| 2,717,232 | 9/1955 | Geller et al. | 203/14 |
| 3,493,473 | 2/1970 | Naito et al. | 546/353 |
| 3,584,737 | 6/1971 | Giesselmann et al. | 546/353 |
| 3,804,722 | 4/1974 | Oliver | 203/14 |

FOREIGN PATENT DOCUMENTS

| | | | |
|---|---|---|---|
| 257257 | 6/1988 | German Democratic Rep. | 546/353 |
| 2-193967 | 7/1990 | Japan | 546/353 |
| 1315452 | 6/1987 | U.S.S.R. | 546/353 |

*Primary Examiner*—Wilbur Bascomb, Jr.

[57] ABSTRACT

Pyridine cannot be completely separated from water by conventional distillation or rectification because of the minimum boiling azeotrope. Pyridine can be readily separated from water by using azeotropic or extractive distillation. Typical examples of effective agents are: by azeotropic distillation, methyl isoamyl ketone and propylene glycol dimethyl ether; by extractive distillation, isophorone and sulfolane.

2 Claims, No Drawings

SEPARATION OF PYRIDINE FROM WATER BY EXTRACTIVE DISTILLATION

FIELD OF THE INVENTION

This invention relates to a method for separating pyridine from water using certain organic compounds as the agent in azeotropic or extractive distillation.

DESCRIPTION OF PRIOR ART

Extractive distillation is the method of separating close boiling compounds or azeotropes by carrying out the distillation in a multi-plate rectificate column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Pyridine, B.P.=115° C. forms a minimum boiling azeotrope with water at 94° C. containing 43% water. The pyridine-water azeotrope is impossible to separate by distillation because the relative volatility is 1.0. Extractive distillation would be an attactive method of effecting the separation of pyridine from water if agents can be found that (1) will enhance the relative volatility between pyridine and water and (2) are easy to recover, that is, form no azeotrope with pyridine or water and boil sufficiently above these two to make separation by rectification possible with only a few theoretical plates. Azeotropic distillation would also be an attractive method of separating these two if agents can be found that will enhance the relative volatility sufficiently.

The advantage of using azeotropic or extractive distillation in this separation can be seen from the data presented in Table 1 below.

TABLE 1

| Theoretical And Actual Plates Required vs. Relative Volatility | | |
|---|---|---|
| Relative Volatility | Theoretical Plates Required At Total Reflux, 99% Purity | Actual Plates Required, 75% Eff. |
| 1.2 | 52 | 70 |
| 1.5 | 23 | 31 |
| 2.0 | 13 | 17 |
| 2.5 | 10 | 13 |

The relative volatility of the pyridine-water azeotrope is 1 and thus cannot be separated by conventional rectification. Plates possessing an efficiency of 75% are commonly employed. Several of the agents that we have discovered yield a relative volatility of 2.0 or higher which would require a plate requirement of only 17.

Extractive distillation typically requires the addition of an equal amount to twice as much extractive agent as the pyridine-water mixture on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable also that the extractive agent be miscible with the pyridine otherwise it will form a two-phase azeotrope with the pyridine in the recovery column and some other method of separation will have to be employed.

OBJECTIVE OF THE INVENTION

This objects of this invention are to provide a process or method of azeotropic or extractive distillation that will enhance the relative volatility of pyridine from water in their separation in a rectification column. It is a further object of this invention to identify organic compounds that are stable, can be separated from the pyridine by rectification with relatively few plates and can be recycled to the extractive distillation column with little decomposition.

SUMMARY OF THE INVENTION

The objects of this invention are provided by a process for the separation of pyridine from water which entails the use of certain organic compounds as the agent in azeotropic or extractive distillation.

DETAILED DESCRIPTION OF THE INVENTION

We have discovered that certain organic compounds will effectively increase the relative volatility between pyridine and water and permit the separation of pyridine from water by rectification when employed as the agent in azeotropic or extractive distillation. Table 2 lists the agents that we have found to be effective azeotrope formers to recover water as the overhead from pyridine. The data in Table 2, 3, 4 and 5 was obtained in a vapor-liquid equilibrium still. In every case, the starting material was the pyridine-water azeotrope. The relative volatilities are listed for each of the agents. The compounds which are effective azeotrope formers to remove water as overhead from pyridine are methyl isoamyl ketone, methyl isobutyl ketone, amyl formate and 4-methyl-2-pentanone. Propylene glycol dimethyl ether brings out the pyridine as overhead product. Table 3 lists the compounds that we have found to be effective extractive distillation agents to separate water and pyridine. The compounds which are effective in removing water as overhead product are isophorone, ethylene glycol, propylene glycol, sulfolane, adiponitrile, propylene carbonate, propoxypropanol, butoxypropanol, dipropylene glycol methyl ether, 2,4-pentanedione, ethylene glycol methyl ether, ethylene glycol ethyl ether, ethylene glycol butyl ether, ethylene glycol hexyl ether, 2-methoxyethyl acetate, ethylene glycol diacetate, diethyl ethanol amine, phenol, acetic acid, propionic acid, glyceryl triacetate and 2-methyl-1,3-propanediol. The compounds which are effective in removing pyridine as overhead product are dimethylsulfoxide, ethanol amine and 1,3-butanediol.

Table 4 lists a number of compounds that proved to be ineffective as extractive distillation agents in the separation of pyridine from water.

Two of the agents whose relative volatility had been determined in the vapor-liquid equilibrium still were then evaluated in a glass perforated plate rectification column possessing 7.3 theoretical plates and the results listed in Table 5. Isophorone gave a relative volatility of 1.26 after only one hour of operation. Sulfolane gave a relative volatility of 1.4 after two hours of continuous operation.

THE USEFULNESS OF THE INVENTION

The usefulness or utility of this invention can be demonstrated by referring to the data presented in Tables 2 to 5. All of the successful agents show that pyridine can be separated from water by means of azeotropic or extractive distillation in a rectification column and that the ease of separation as measured by relative volatility is considerable.

TABLE 2

Effective Azeotropic Agents For Separating Water From Pyridine

| Compounds | Relative Volatility |
| --- | --- |
| Methyl isoamyl ketone | 2.2 |
| Methyl isobutyl ketone | 1.8 |
| 4-Methyl-2-pentanone | 2.1 |
| Amyl formate | 1.3 |
| Propylene glycol dimethyl ether | 1.5* |

*Brings pyridine out as overhead

TABLE 3

Effective Extractive Agents For Separating Water From Pyridine

| Compounds | Relative Volatility |
| --- | --- |
| Isophorone | 1.3 |
| Dimethylsulfoxide | 1.6* |
| Ethylene glycol | 2.8 |
| Propylene glycol | 1.7 |
| Sulfolane | 1.4 |
| Adiponitrile | 1.5 |
| Propylene carbonate | 1.2 |
| Propoxypropanol | 1.3 |
| Ethanol amine | 2.6* |
| Butoxypropanol | 1.9 |
| Dipropylene glycol methyl ether | 1.3 |
| 2,4-Pentanedione | 1.7 |
| Ethylene glycol methyl ether | 1.3 |
| Ethylene glycol ethyl ether | 2.2 |
| Ethylene glycol butyl ether | 1.9 |
| Ethylene glycol hexyl ether | 1.5 |
| 2-Methoxyethyl acetate | 1.6 |
| Ethylene glycol diacetate | 1.3 |
| Diethyl ethanol amine | 1.2 |
| Phenol + Dimethylsulfoxide | 2.3 |
| Acetic acid | 1.4 |
| Propionic acid | 1.8 |
| Glyceryl triacetate | 1.4 |
| 1,3-Butanediol | 4.9* |
| 2-Methyl-1,3-propanediol | 1.4 |

*Brings pyridine out as overhead

TABLE 4

Ineffective Agents For Separating Water From Pyridine

| | |
| --- | --- |
| Dimethylformamide | 1,4-Butanediol |
| 1,2-Butanediol | 1,5-Pentanediol |
| 1,6-Hexanediol | Diethylene glycol |
| Dipropylene glycol | Polyethylene glycol 200 |
| Ethyl aceto acetate | Polyethylene glycol 300 |
| Diisobutyl ketone | Diethylene glycol diethyl ether |
| Dimethylacetamide | 2-Methyl pyrrolidone |
| Ethylene cyanohydrin | Diethyl ethanol amine |
| Morpholine | Tetrahydro furfuryl alcohol |
| Diethylene glycol ethyl ether | Diethylene glycol methyl ether |
| N-Methyl ethanol amine | Diethylene glycol dimethyl ether |

TABLE 5

Data From Runs Made In Rectification Column - Water From Pyridine

| Agent | Column | Time hrs. | Weight % Water | Weight % Pyridine | Relative Volatility |
| --- | --- | --- | --- | --- | --- |
| Isophorone | Overhead | 1 | 82.5 | 17.5 | 1.26 |
| | Bottoms | | 46 | 54 | |
| " | Overhead | 2 | 82.7 | 17.3 | 1.26 |
| | Bottoms | | 47.1 | 52.9 | |
| Sulfolane | Overhead | 1 | 73.1 | 26.9 | 1.12 |
| | Bottoms | | 54.3 | 45.7 | |
| " | Overhead | 2 | 92.2 | 7.8 | 1.40 |
| | Bottoms | | 51.5 | 48.5 | |

WORKING EXAMPLES

EXAMPLE 1

Eighty grams of the pyridine-water azeotrope and 30 grams of methyl isoamyl ketone as the azeotrope former were charged to a vapor-liquid equilibrium still and refluxed for seven hours. Analysis indicated a vapor composition of 69.4% water, 30.6% pyridine; a liquid composition of 50.9% water, 49.1% pyridine which is a relative volatility of 2.2.

EXAMPLE 2

Eighty grams of the pyridine-water azeotrope and 30 grams of propylene glycol dimethyl ether as the azeotrope former were charged to the vapor-liquid equilibrium still and refluxed for three hours. Analysis indicated a vapor composition of 34.6% water, 17.5% pyridine, 47.9% agent; a liquid composition of 65.8% water, 22.4% pyridine and 11.8% agent which is a relative volatility of pyridine to water of 1.5.

EXAMPLE 3

A solution comprising 228 grams of pyridine and 172 grams of water was placed in the stillpot of a 7.3 theoretical plate glass perforated plate column. When refluxing began, an extractive agent comprising sulfolane was pumped into the top of the column at a rate of 15 ml/min. The temperature of the extractive agent as it entered the column was 85° C. After establishing the feed rate of the extractive agent, the heat input to the pyridine-water in the stillpot was adjusted to give a total reflux rate of 40 ml/min. After two hours of operation, overhead and bottoms samples of approximately two ml. were collected and analysed by gas chromatography. The overhead analysis was 92.2% water, 7.8% pyridine and the bottoms analysis was 51.5% water, 48.5% pyridine. Using these compositions in the Fenske equation, with the number of theoretical plates in the column being 7.3, gave an average relative volatility of 1.4 for each theoretical plate. This data is presented in Table 5.

We claim:

1. A method for recovering pyridine from a mixture of pyridine and water which comprises distilling a mixture of pyridine and water in the presence of about one part of an extractive agent per part of pyridine-water mixture, recovering water as overhead product and obtaining the pyridine and the extractive agent from the stillpot, wherein said extractive agent consists of one material selected from the group consisting of isophorone, ethylene glycol, propylene glycol, sulfolane, adiponitrile, propylene carbonate, propoxypropanol, butoxypropanol, dipropylene glycol methyl ether, 2,4-pentanedione, ethylene glycol methyl ether, ethylene glycol ethyl ether, ethylene glycol butyl ether, ethylene glycol hexyl ether, 2-methoxyethyl acetate, ethylene glycol diacetate, diethyl ethanol amine, acetic acid, propionic acid, glyceryl triacetate and 2-methyl-1,3-propanediol.

2. A method for recovering pyridine from a mixture of pyridine and water which comprises distilling a mixture of pyridine and water in the presence of about one part of an extractive agent per part of pyridine-water mixture, recovering pyridine as overhead product and obtaining the water and the extractive agent from the stillpot, wherein said extractive agent consists of one material selected from the group consisting of dimethylsulfoxide, ethanol amine and 1,3-butanediol.

* * * * *